(12) United States Patent
Hely et al.

(10) Patent No.: US 6,189,532 B1
(45) Date of Patent: *Feb. 20, 2001

(54) VALVE FOR USE IN A GAS DELIVERY SYSTEM

(75) Inventors: Kenneth Frederick Hely, Grasmere; Perry David Lithgow, North Ryde, both of (AU)

(73) Assignee: ResMed Limited, North Ryde (AU)

( * ) Notice: Under 35 U.S.C. 154(b), the term of this patent shall be extended for 0 days.

This patent is subject to a terminal disclaimer.

(21) Appl. No.: 09/300,750

(22) Filed: Apr. 26, 1999

Related U.S. Application Data

(63) Continuation of application No. 08/772,285, filed on Dec. 20, 1996, now Pat. No. 5,896,857.

(30) Foreign Application Priority Data

Dec. 16, 1996 (AU) ....................................... 04229

(51) Int. Cl.[7] .................................................. A62B 9/02
(52) U.S. Cl. ................... 128/205.24; 128/203.11
(58) Field of Search ........................... 128/203.11, 205.24

(56) References Cited

U.S. PATENT DOCUMENTS

| | | | | |
|---|---|---|---|---|
| 4,449,525 | * | 5/1984 | White et al. | 128/203.11 |
| 4,579,114 | * | 4/1986 | Gray et al. | 128/203.11 |
| 5,230,330 | * | 7/1993 | Price | 128/203.11 |
| 5,878,743 | * | 3/1999 | Zdrojkowski et al. | 128/204.23 |
| 5,881,722 | * | 3/1999 | Devries et al. | 128/205.24 |
| 5,896,857 | * | 4/1999 | Hely et al. | 128/205.24 |
| 5,950,623 | * | 9/1999 | Michell | 128/204.24 |
| 6,032,667 | * | 3/2000 | Heinonen | 128/205.24 |
| 6,055,981 | * | 5/2000 | Laswick et al. | 128/205.24 |

* cited by examiner

*Primary Examiner*—Aaron J. Lewis
(74) *Attorney, Agent, or Firm*—Pillsbury Madison & Sutro LLP

(57) ABSTRACT

A safety valve for use in closed systems wherein there is a flow generator delivering oxygen or some other type of breathing gas to a patient. The safety valve of the present invention vents to the open atmosphere in the event that the breathing gas generated by the flow generator diminishes or terminates.

10 Claims, 9 Drawing Sheets

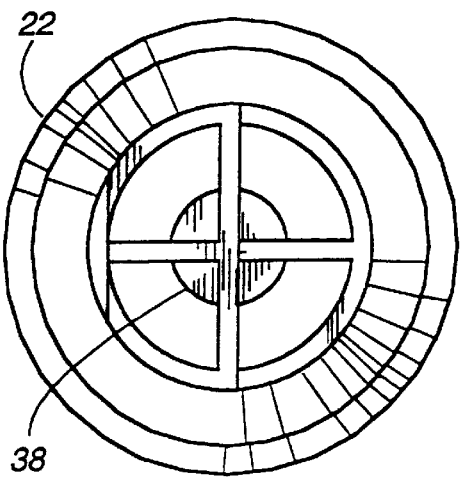
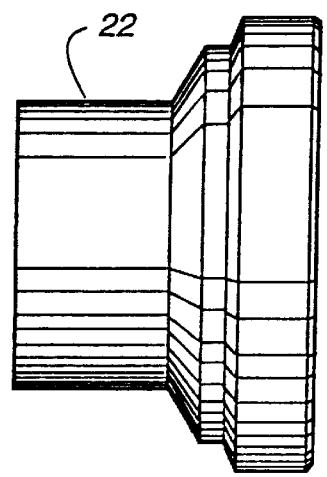
Fig. 6        Fig. 7
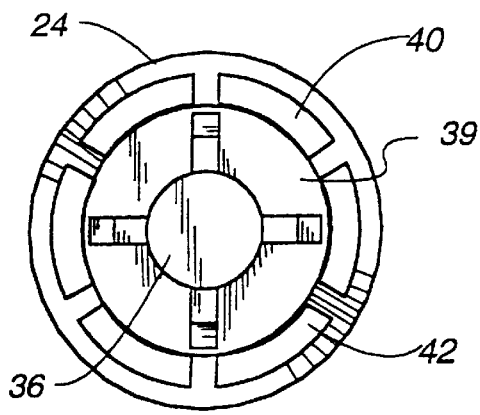
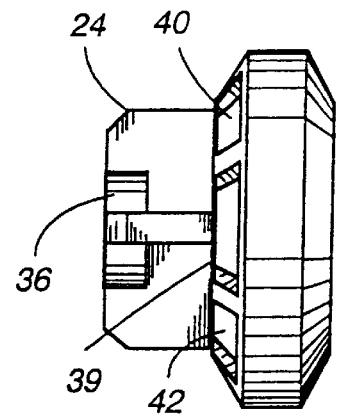
Fig. 8        Fig. 9
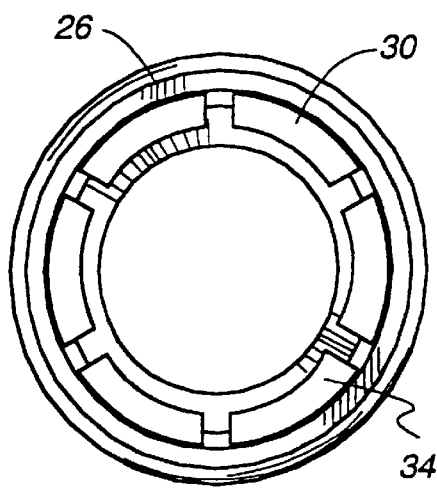
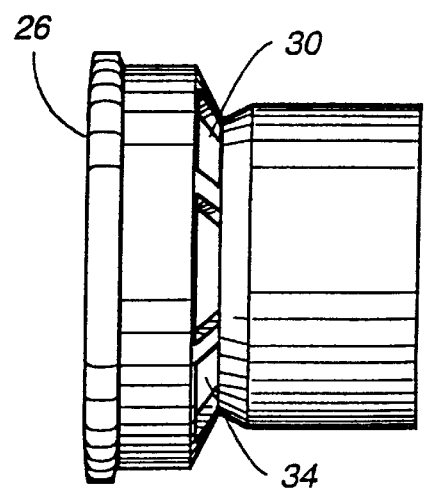
Fig. 10       Fig. 11

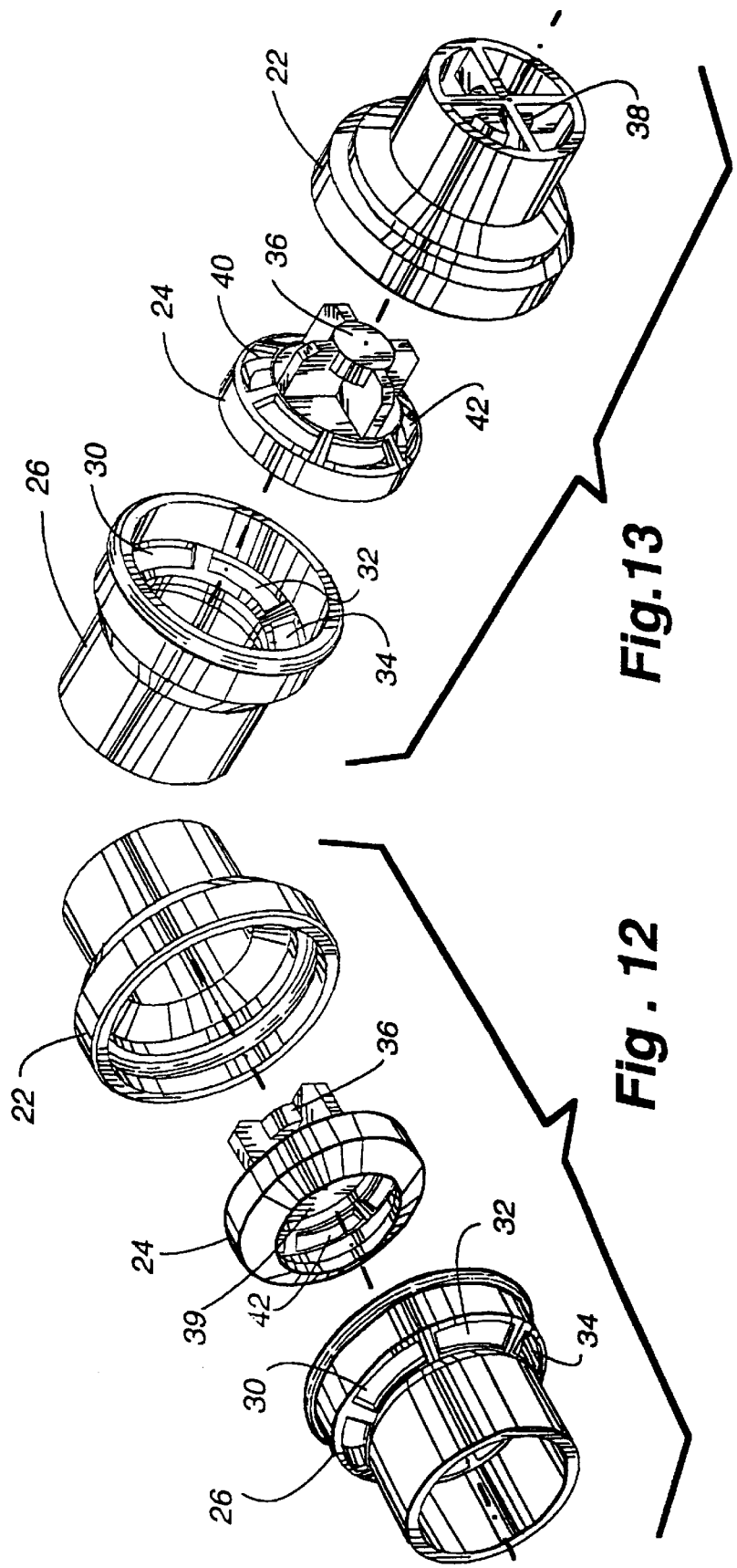

VALVE FOR USE IN A GAS DELIVERY SYSTEM

This is a continuation of application Ser. No. 08/722,285, filed on Dec. 20, 1996 U.S. Pat. No. 5,896,857 which is hereby incorporated in its entirety.

FIELD OF THE INVENTION

The present invention relates to a valve for use in an oxygen or gas delivery system. In particular, the valve provides a safety mechanism wherein if a system which delivers oxygen or gas to a patient through a mask becomes dysfunctional, the valve opens to the atmospheric environment.

BACKGROUND OF THE INVENTION

Nasal masks currently are employed for various purposes, including the delivery of oxygen to persons who suffer from lung disease or who are exposed to rarefied atmospheres, for administering anesthetic gases and for delivering pressurized air to persons who suffer from disorders such as sleep apnea. The masks usually are molded from a relatively soft, resilient, elastic material and they are shaped during manufacture to match the facial contours of an average intended wearer. However, a problem with the known types of masks is that, because individuals vary so much from the average, the masks must be forced against their inherent resiliency to deform and so adapt to the shapes of the users in order to avoid gas leakage. This requires that the masks be secured firmly by retaining straps or harnesses in order to prevent air leakage.

Flow generators are typically utilized to deliver a breathable gas to a patient wearing a mask. The flow generator is generally connected to flexible tubing which is secured to a mask worn by a patient. If the flow generator's operation is interrupted as a result of a power outage or other mechanical or electrical failure, there may be a significant build up of carbon dioxide in the mask as the patients exhaled air is not washed out of outlet vents which are usually contained in the mask. This may present a health problem to the patient. Additionally, when oxygen is being delivered in a closed system by a flow generator, and there is a failure of the flow generator, oxygen may still be delivered. If and when power is restored to the flow generator, there may be a significant amount of oxygen present in the flow generator creating a possible explosion hazard. Finally, there are often humidifiers used with flow generators. Any water from the humidifier should be prevented from entering the generator.

There have been numerous patents which have addressed some sort of safety valve for gas or air delivery masks. An example of such a patent is U.S. Pat. No. 5,438,981. This patent utilizes a counter balanced, rigid valve element which depending on the gas flow, either covers an opening to the ambient air or covers the gas flow airway such that the air or breathing gas is forced out into the ambient air opening. However, this system suffers from being a fairly complicated and expensive system which must rely on a counter balanced moving part. Additionally, if any condensation from the air gets on or around the balanced valve element, the operation of this valve element may be compromised. Finally, this valve is difficult to clean.

Thus, there is a need for a valve with fewer moving parts and easier operation in the event of moisture or condensation entering the valve element.

SUMMARY OF THE INVENTION

The present invention is a slider valve element with a hollow or vented housing aligned with inlet orifices and exhaust vents. A returning force, such as a magnet or coil spring, is used to return the vented slide element to its resting position when the inlet orifices are blocked. When the air flow is applied to the inlet, the returning force is overcome wherein the slider element is pushed up to block the exhaust vents. Thereafter, the air flows through the slider and into the mask or tubing to provide therapy to the patient. If the airflow from the flow generator or air source is taken away, the returning force returns the slider element to block the inlet airway passage and thus opens the exhaust vent to the atmosphere. The valve is designed to fit directly onto a mask frame elbow and/or tubing and/or the outlet of the flow generator. There may also be multiple valves in a single system.

BRIEF DESCRIPTION OF THE DRAWINGS

FIG. 6 is an end view of one of the valve elements shown in FIG. 5.

FIG. 7 is a side view of the valve element shown in FIG. 6.

FIG. 8 is an end view of one of the elements shown in FIG. 5.

FIG. 9 is a side view of the element shown in FIG. 8.

FIG. 10 is an end view of one of the elements shown in FIG. 5.

FIG. 11 is a side view of the element shown in FIG. 10.

FIG. 12 is an exploded perspective view of FIG. 5.

FIG. 13 is an exploded perspective from the other end of that shown in FIG. 12.

DETAILED DESCRIPTION OF THE PREFERRED EMBODIMENT

Figure 1:
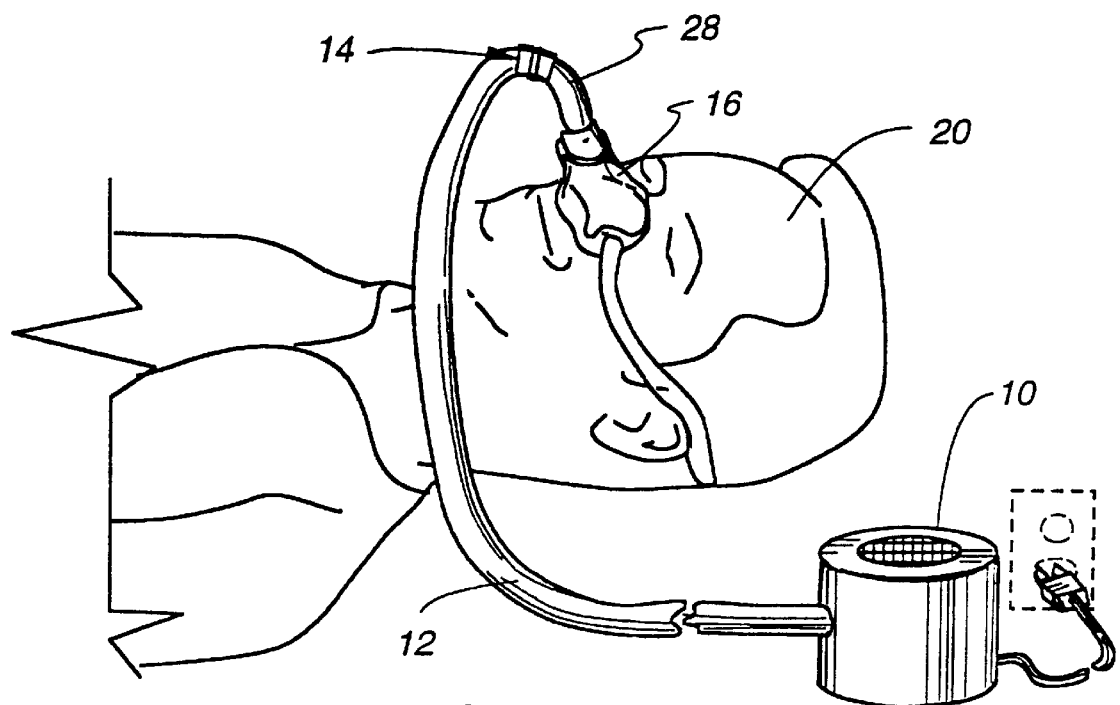
FIG. 1 is a general schematic drawing of a system comprising a flow generator being connected to a valve and mask via tubing in which the mask is connected to a patient.

The present invention can be used for any air or oxygen delivery system wherein there is some type of flow generator hooked up to a tube or airflow conduit which is thereafter secured to a mask which is secured to a patient. The gas being transmitted can be any type of breathing or therapeutic gas. The general schematic of this is shown in FIG. 1 wherein there is a flow generator 10 having an air flow tube 12 secured to a schematic of the valve of the present invention 14 which is thereafter connected to a mask 16 of a patient 20. The mask shown is just an example of numerous types of breathing-patient interfaces. Although the present invention's valve can be used for any type of closed air delivery system, it is preferably used in CPAP applications. CPAP, continuous positive airway pressure, is a therapy developed by Dr. Colin Sullivan, as described in U.S. Pat. No. 4,944,310 which treats, among other things, the sleep disorder of sleep apnea. CPAP therapy requires pressurized air delivered out of flow generator, such as that shown as 10 in FIG. 1, to a patient 20. Pressurized air acts to force open the air passages of a patient, thus preventing the temporary occlusion of airway passages which are typical in sleep apnea patients.

Figure 14:
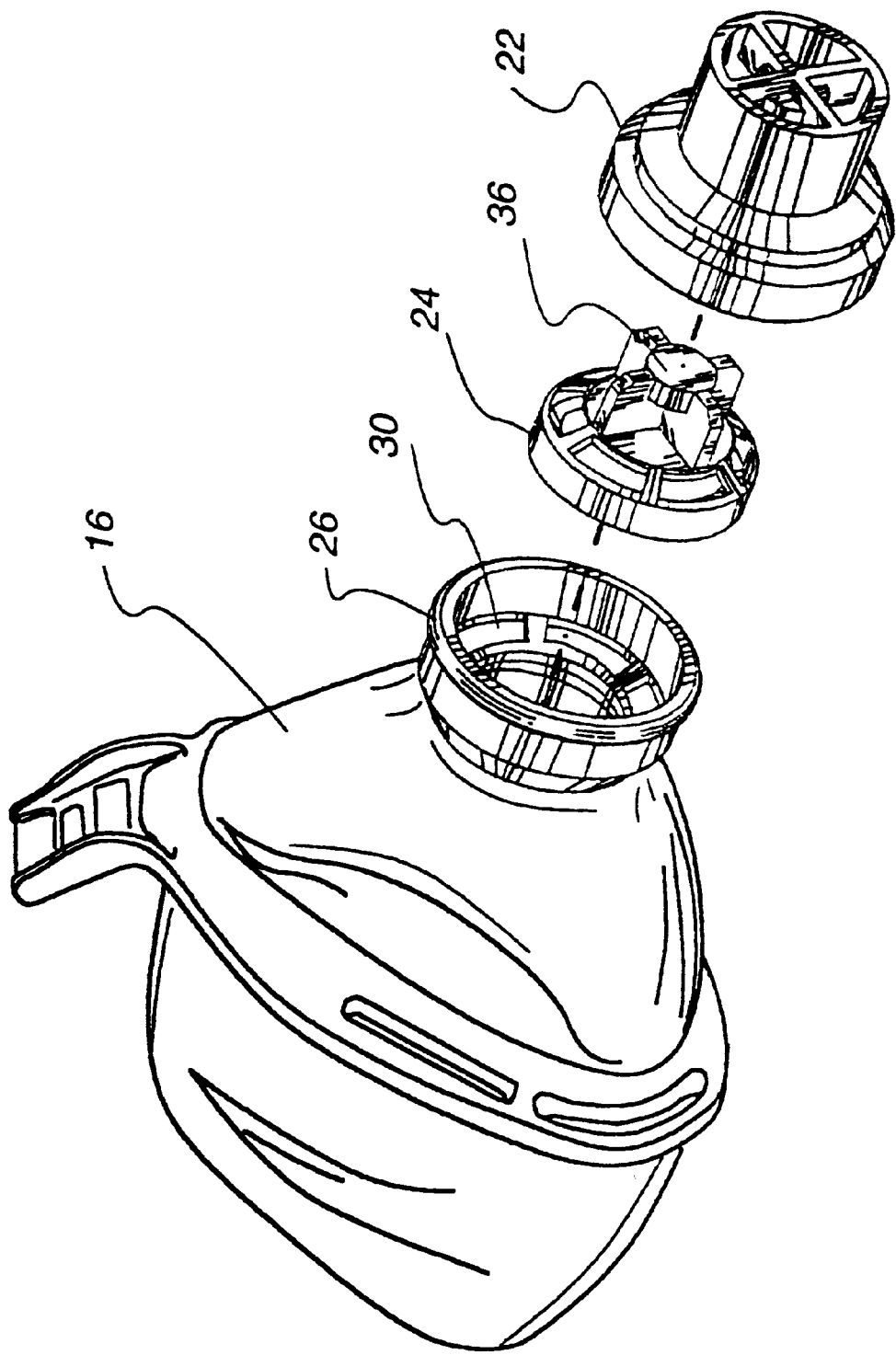
FIG. 14 is an exploded view of an alternate embodiment of the present invention wherein the valve is incorporated into the mask.
Figure 15:
FIG. 15 is a perspective view of an alternative embodiment of the present invention wherein the valve is incorporated into the mask.

The location of the valve 14 shown in FIG. 1 is just one example of a location under this invention. Valve 14 could be connected to mask 16, or it could be an integral part of mask 16, as shown in FIGS. 14 and 15. It also could be located at the outlet of the flow generator 10. There could also be two or more valves located on a single system. It is preferred to put the valve 14 as close to the mask 16 as possible, or to make it part of the mask 16.

The flow generator 10 can be a CPAP flow generator, bottled gas, a respirator, or any other type of device that delivers breathable, therapeutic, or anesthetic gas.

Figure 2:
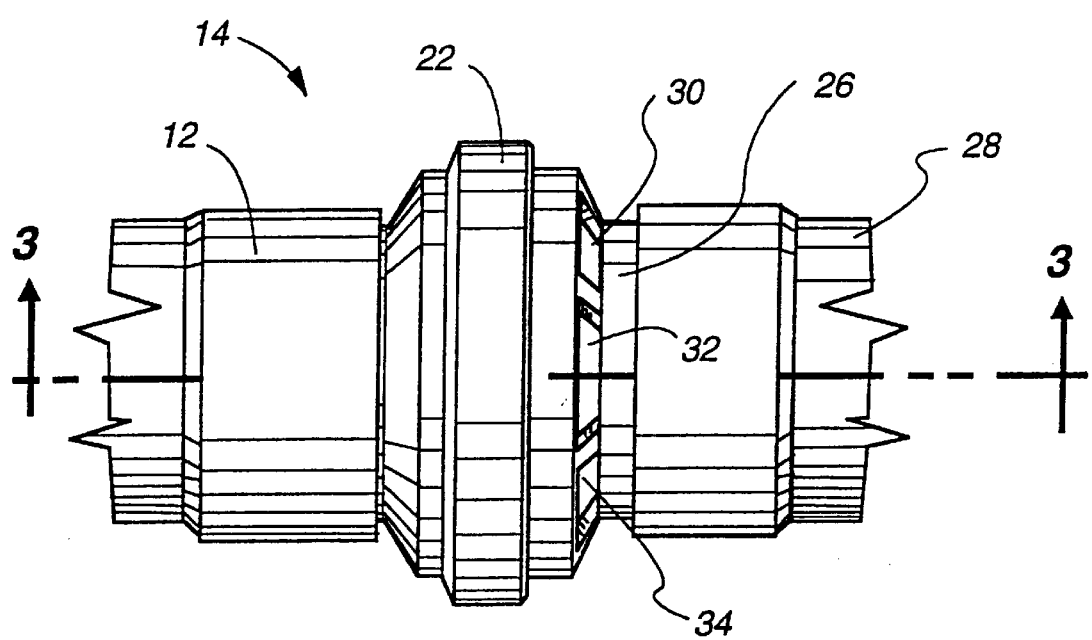
FIG. 2 is a side view of a valve of the present invention.
Figure 3A:
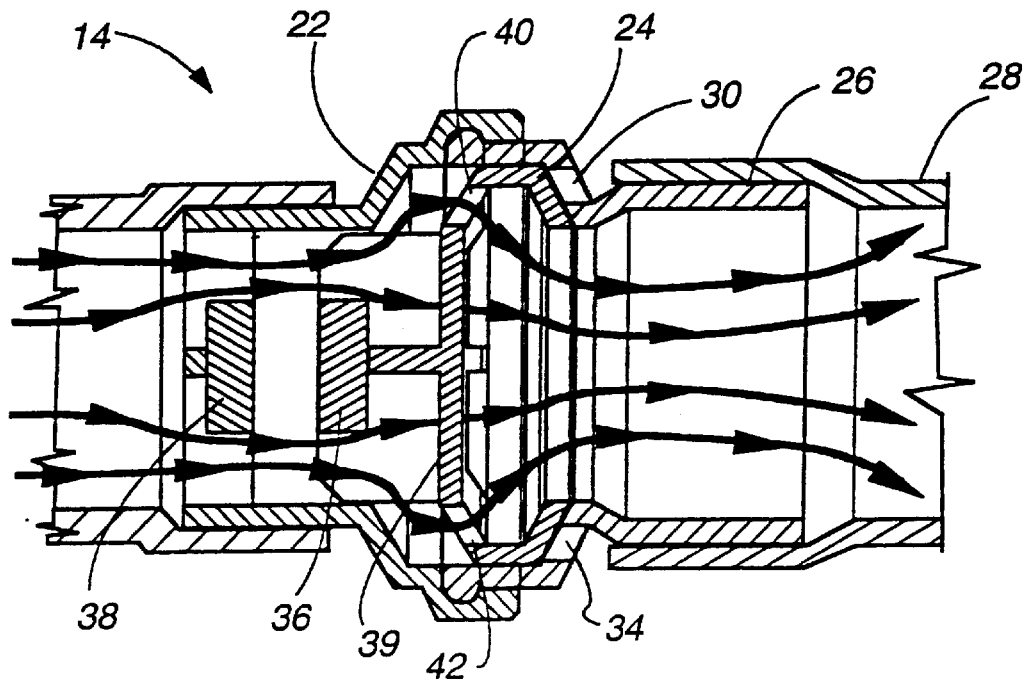
FIG. 3A is the cross sectional view of FIG. 3 with airflow from the flow generator being shown.
Figure 3:
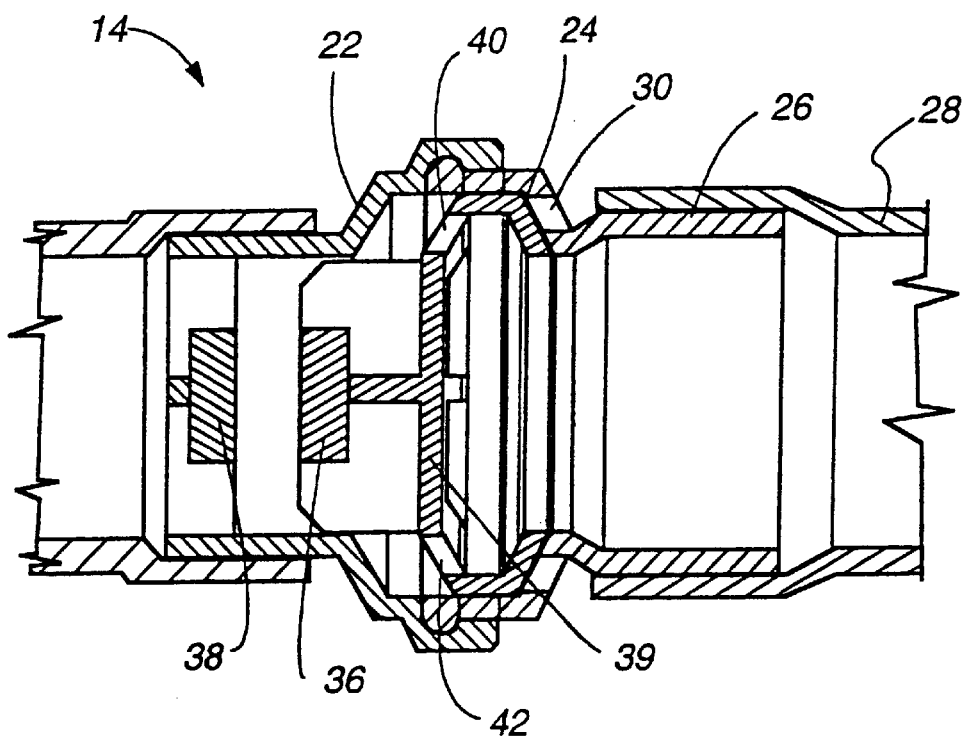
FIG. 3 is a cross sectional view of the figure of FIG. 2.
Figure 4A:
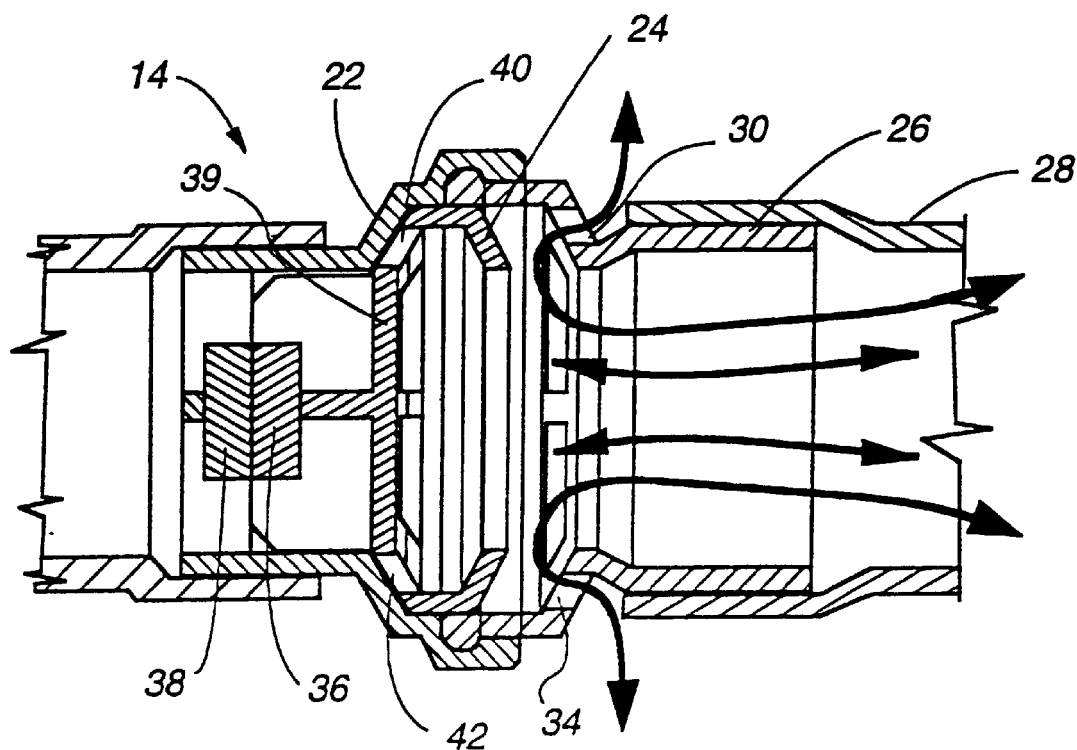
FIG. 4A is the view of FIG. 4 wherein the direction of air is illustrated with the use of arrows.
Figure 4:
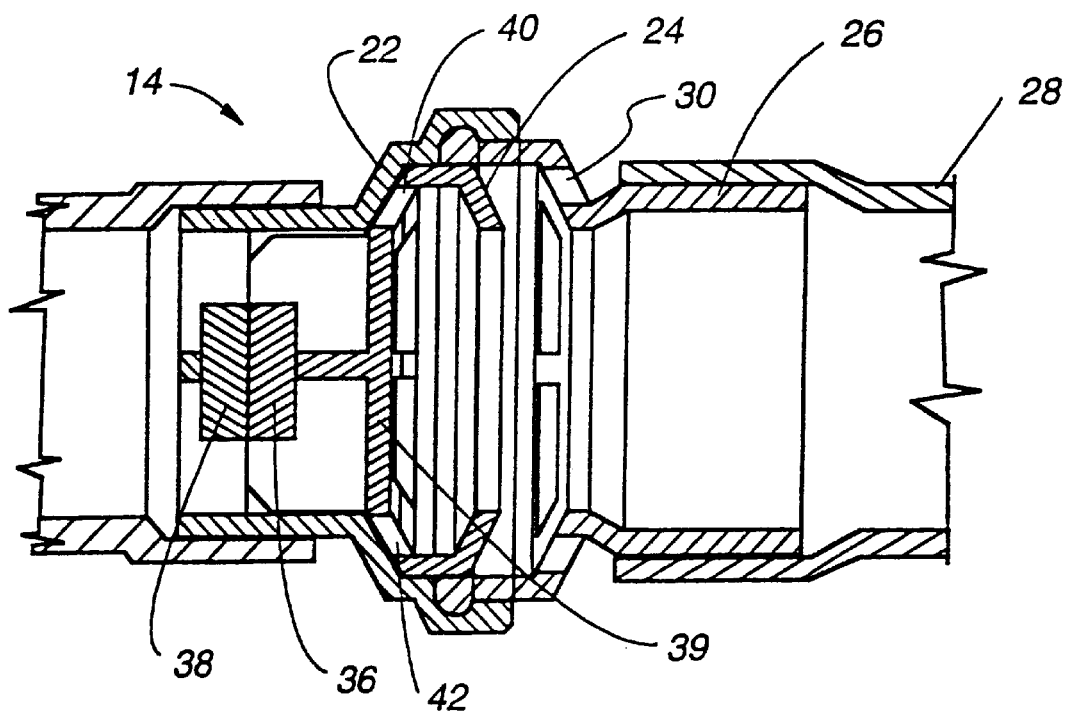
FIG. 4 is a cross sectional view of the valve of the present invention wherein the flow of air from the generator has stopped.
Figure 5:
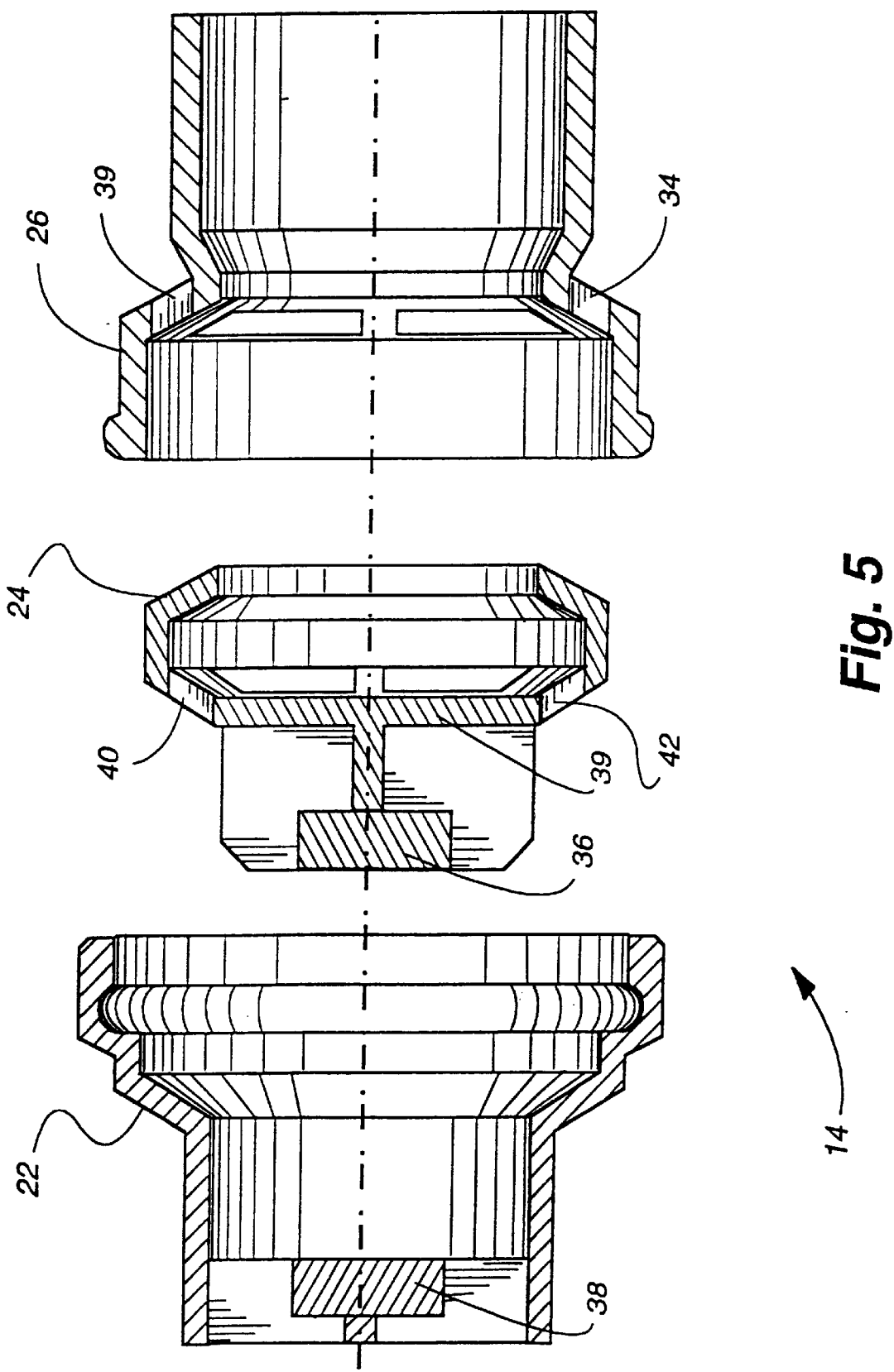
FIG. 5 is an exploded view of the valve shown in FIGS. 2–4.

FIG. 2 is a close up of the valve 14 shown in FIG. 1, which is more easily seen in FIG. 5. The valve in FIG. 2 has three parts. It has what will be referred to as a flow generator housing or means to deliver gas housing 22, slider element 24 (visible in FIGS. 3, 3A, 4, 4A, 8, 9, 12, and 13) and mask housing 26. The normal air flow for the valve 14 shown in FIGS. 2 and 3A comes from a flow generator located from the direction of the flow generator housing 22 wherein it passes through the flow generator housing 22, through valve element 24 through mask housing 26 and into tube 28. During the normal operation wherein the flow generator is generating a flow of gas, the ports identified as 30, 32 and 34 are closed to the open air, and the air flows right through the valve 14 into tubing 28 wherein the air flows into the mask shown as 16 in FIG. 1. This airflow is best shown in FIG. 3A wherein the arrows indicate the airflow. The airflow comes through tube 12, into flow generator housing 22, whereby it enters the slider element portion of the valve 24.

The slider element 24 has at least two positions. The two positions are shown in FIGS. 3A and 4A. In FIG. 3A, slider valve element 24 is forced open by the airflow. The airflow overcomes the returning force generated by, in the preferred embodiment, magnets located at 36 and 38. The magnetic force imparted to the slider element 24 by magnets 36 and 38 is a very slight force, which is overcome by the flow of air shown in FIG. 3A. Generally, this will be referred to as the returning force which acts to close the slider valve 24 in the event of decreased air flow. This returning force means can be any type of force which imparts a force on the slider valve 24 to close in the event that airflow is terminated or diminished. A preferred force is a magnetic force, but the use of springs, electro magnetic pulses, elastic materials, gravity, or other biasing forces are non-limiting examples of other types of forces which could be used. These are merely examples of biasing forces, and it is envisioned that other structural mechanisms could be implemented which would close the slider valve 24 in the event that airflow is terminated or slowed to the extent that not enough air is delivered to the patient. It is important to note that the airflow from the flow generator 10 does not have to be terminated, but rather if there is decreased airflow, which might be insufficient to satisfy the pulmonary needs of the patient, the valve might close as well.

During normal operation, the airflow from the generator 10 flows around what is identified as base plate 39 of the slider valve 24. This base plate 39 is a structure on which a component of the returning force may be secured onto the slider valve 24. The returning force may be located or secured at positions other than the base plate 39. The air flows around said base plate 39, and it also flows through port holes 40 and 42. It is important to note that there could be a single port hole, or a multitude of port holes. Thereafter, the air flows into mask housing 26 then tube 28 which leads to the mask of the patient or in another embodiment, directly from the valve 24 into mask 16. The terms "flow generator housing" and "mask housing" are not meant to assert that these housings are part of the flow generator or mask. Rather, this is merely to indicate the position of the valve housing, e.g., the flow generator housing means that part of the valve housing which is closest to the flow generator 10 and the mask housing is that portion of the valve housing which is closest to the mask 16. However, the housings can be a part of the mask 16 or flow generator 10 in embodiments that fall within the scope of this invention. This would include the valve being an integral part of the mask 16 or flow generator 10, which means there is no tubing connecting the valve to either the mask or flow generator.

FIG. 4A illustrates the slider valve element 24 wherein the airflow from the flow generator has diminished to the point where it does not override the attractive or biasing force pulling the slider valve element 24 closed. What occurs in FIGS. 4 and 4A is the force of the air which had originally been pushing on base plate 39 keeping the valve 14 open has decreased to a point such that the attraction of the two magnets 36 and 38 is not overcome anymore. The slider valve 24 then moves to the left, thereby closing off the ability of the air to flow freely between the flow generator and the mask. In the preferred embodiment, both 36 and 38 are magnets. However, as described above, there are many options, and the other options would be that one of the elements, e.g., 36 would be a magnet wherein element 38 would merely be some material capable of being attracted to a magnet, such as iron, or an iron composite. As shown in FIG. 4a, the airflow would thus occur through ports 30 and 34. In this mode, the patient 20 is breathing on his or her own, and the air is flowing in both directions, and is open to the atmosphere through ports 30 and 34. As is shown in later figures, there are many ports, thus the flow of oxygen or any gas moves quite freely through the ports 30, 32 and 34, into the mask housing 26 and into the patient's respiratory system.

FIG. 5 is an exploded view of the valve shown in FIGS. 1–4. Although FIG. 5 shows essentially three separate components, it is envisioned that just 2 components could be used, wherein the slider valve 24 fits within flow generator housing 22, which would be molded to achieve the general structure of mask housing 26. In other words, there would be a one piece outer housing, which would essentially be a combination of housings 22 and 26 wherein slider element 24 would be contained therein. However, this construction might be more difficult to clean.

FIGS. 6–11 are side and end views of the various elements of the present invention.

FIGS. 12 and 13 are exploded perspective views illustrating the preferred embodiment of the valve of the present invention. As can be seen, the elements are easily molded components preferably out of an engineered polymer or thermoplastic. It is important that the valve can be easily taken apart and thereafter easily reassembled.

FIGS. 14 and 15 illustrate an embodiment which incorporates the valve 14 into the mask 16. This embodiment has the advantage of not needing to make the additional connections of the airflow tube between the mask and the valve.

Figure 16A:
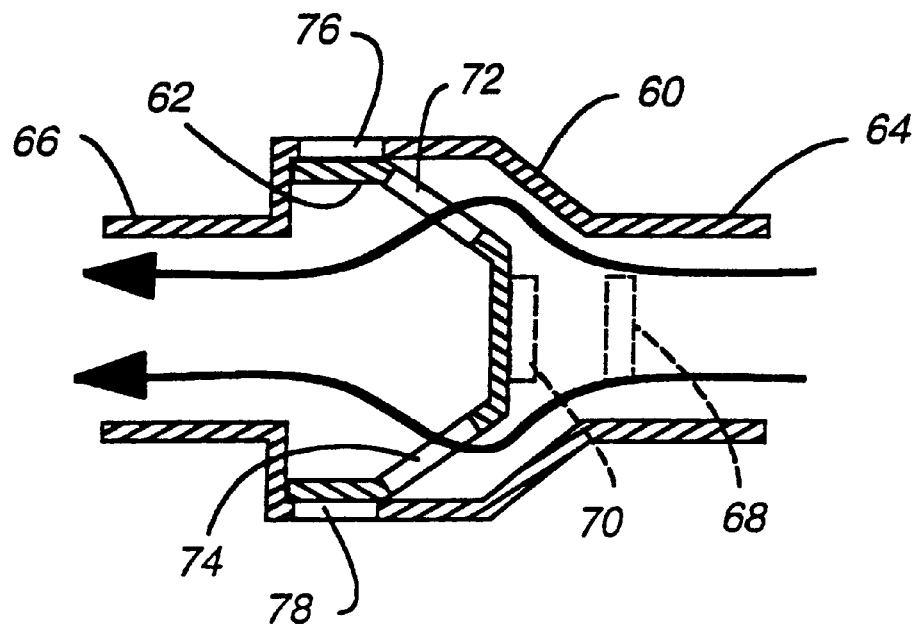
FIG. 16(A) is a cross sectional view of an alternative embodiment of the present invention showing the airflow from the generator to the mask.
Figure 16:
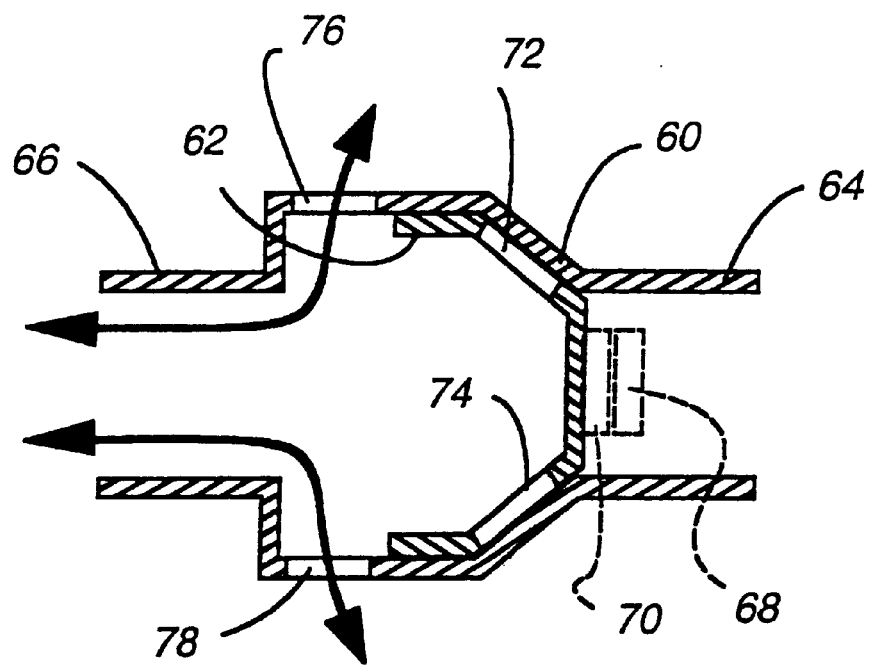
FIG. 16(B) is the alternative embodiment shown in FIG. 14A wherein the flow generator has ceased to operate and the gas flow is from the mask out to the ambient air.

Finally, FIGS. 16(A) and 16(B) illustrate an alternative embodiment of the present invention wherein there are just two elements, that being the outer housing 60 and the slider element 62. FIG. 16(A) illustrates the natural flow wherein the air flows from a generator side 64 to a mask side 66. This flow overcomes some slider element force, which could include the use of the magnetic force disclosed earlier and is shown as magnets 68 and 70 in phantom. Air flows through ports 72 and 74. Once the airflow is lessened or terminated, the returning force is not overcome, wherein FIG. 16(B) illustrates the alternative embodiment of the safety valve of the present invention with the airflow open to the atmosphere, flowing through ports 76 and 78.

The present invention has the advantages of being able to fit all nasal and mouth mask systems. This includes both adults and infants. In the situation of infants, the airflow may be less, and thus the force needed to open the slider valve may be adjusted accordingly. Typically, the slider valve is set such that if pressure falls below about one to three centimeters of water, the valve will vent to the atmosphere. If the airflow pressure is greater than one to three centimeters of water, the slider valve will remain closed to the atmosphere. The valve of the present invention has the advantage of being independent of orientation. That is, although it has to be connected in the right direction between the flow generator and the mask, it can be inverted, held sideways, etc. which often occurs during the time when the patient sleeps. This is an important advantage over the prior valves. Additionally, there are some flow generators which start and stop purposely, such as Resmed's SmartStart and Autoset flow generators and the present invention can accommodate such starting and stopping wherein the slider valve element will open and close accordingly.

The present valve is very easily cleaned, and may be disassembled, cleaned and reassembled very easily both at home or at a hospital or clinic. A humidifier may also be used, and will be attached as a separate device at the flow generator or other location.

The above specification, examples and data provide a complete description of the manufacture and use of the composition of the invention. Since many embodiments of the invention can be made without departing from the spirit and scope of the invention, the invention resides in the claims hereinafter appended.

We claim:

1. A breathing safety valve secured between a patient and means to deliver a breathing gas in a substantially closed system, said safety valve comprising:

(a) an outer housing, said outer housing having a port for the purpose of venting the breathing gas to the atmosphere making the system an open system, and defining a housing shoulder;

(b) a slider element, said slider element defining a slider shoulder and being configured to fit within said outer housing, said slider element having at least two positions engageable within said housing, a first position wherein said slider shoulder engages said housing shoulder to substantially block said port such that said system is closed, and a second position wherein said slider element does not substantially block said port such that said system is open to said atmosphere; and (c) a force mechanism applying a returning force to said slider element, said force biasing said slider element from said first position to said second position.

2. The valve of claim 1 wherein said returning force comprises a first magnet on said slider element and a second magnet on said housing and said first magnet attracts said second magnet.

3. The valve of claim 2 wherein said second position results from said means to deliver a breathing gas not generating said gas in sufficient volume to overcome the returning force created between said magnets.

4. The valve of claim 3, wherein:
   said means to deliver a breathing gas is not generating said gas in sufficient volume to maintain at least one centimeter of pressure in said closed system.

5. The valve of claim 2, wherein:
   said magnets are positioned such that the returning force does not exceed the force applied to said slider element when the atmospheric pressure present in said closed system is about one to three centimeters of water above said atmospheric pressure.

6. The valve of claim 1 wherein said housing comprises two housing parts, a means to deliver gas housing and a mask housing, said mask housing defining said port.

7. The valve of claim 1 wherein said housing has a plurality of ports.

8. The valve of claim 1 wherein said valve is integral with said mask.

9. The valve of claim 1 wherein said valve is integral with said means to deliver a breathing gas.

10. A breathing safety valve secured between a patient and means to deliver a breathing gas in a substantially closed system wherein said valve is integral with said means to deliver a breathing gas, said safety valve comprising:

(a) an outer housing said outer housing having a port for the purpose of venting the breathing gas to the atmosphere;

(b) a slider element, configured to fit within said outer housing, said slider element having at least two positions engageable within said housing, a first position wherein said slider element substantially blocks said port such that said system is closed, and a second position wherein said slider element does not substantially block said port such that said system is open to said atmosphere; and (c) a first magnet on said slider element and a second magnet on said housing to apply a returning force to said slider element, said force biasing said slider element from said first position to said second position.

* * * * *